United States Patent
Geddis et al.

(10) Patent No.: US 9,216,064 B2
(45) Date of Patent: Dec. 22, 2015

(54) SYSTEM FOR CLEANING ROBOTIC SURGICAL INSTRUMENTS

(71) Applicants: David B. Geddis, Dunedin, FL (US); Cheryl J. Geddis, Dunedin, FL (US)

(72) Inventors: David B. Geddis, Dunedin, FL (US); Cheryl J. Geddis, Dunedin, FL (US)

(*) Notice: Subject to any disclaimer, the term of this patent is extended or adjusted under 35 U.S.C. 154(b) by 0 days.

(21) Appl. No.: 14/268,121

(22) Filed: May 2, 2014

(65) Prior Publication Data

US 2015/0313680 A1 Nov. 5, 2015

(51) Int. Cl.
*B08B 3/00* (2006.01)
*A61B 19/00* (2006.01)

(52) U.S. Cl.
CPC ........................................ *A61B 19/34* (2013.01)

(58) Field of Classification Search
CPC ................................ A61B 1/123; A61B 19/34
See application file for complete search history.

(56) References Cited

U.S. PATENT DOCUMENTS

| | | | |
|---|---|---|---|
| 5,630,436 A | 5/1997 | Chase | |
| 2004/0118440 A1* | 6/2004 | Sasaki et al. | 134/166 C |
| 2007/0005002 A1* | 1/2007 | Millman | A61B 19/2203 604/30 |

OTHER PUBLICATIONS

Surgisonic® Ultrasonic Cleaner for Tubular Surgical Instruments.*
SurgiSonic(r) Untrasonic Cleaner for Tubular Surgical Instruments, Copyright 2010 Geddis Incorporated—see p. 4 for flow-through method of cleaning instruments that do not have seals.

* cited by examiner

*Primary Examiner* — Michael Barr
*Assistant Examiner* — Jason Riggleman
(74) *Attorney, Agent, or Firm* — Larson & Larson, P.A.; Frank Liebenow; Patrick Reid

(57) ABSTRACT

An apparatus for cleaning robotic surgical instruments includes an ultrasonic emersion tank having cleaning fluid there within and a device for providing negative pressure or suction (e.g. a pump) through a tool-end cleaning chamber. Cleaning fluid is drawn into the tool-end cleaning chamber through a plurality of intake holes in the tool-end cleaning chamber by the suction, thereby creating turbulence and flow around an end of a robotic surgical instrument that is positioned in the tool-end cleaning chamber. Cleaning of the shaft and control box of the robotic surgical instrument is performed by providing negative pressure or suction to a port on the control box of the robotic surgical instrument.

11 Claims, 4 Drawing Sheets

SYSTEM FOR CLEANING ROBOTIC SURGICAL INSTRUMENTS

FIELD

This invention relates to the field of cleaning robotic surgical instruments after use in surgery, and in particular to an adaptation of a suction apparatus system that makes it possible to individually clean both the distal and proximal segmented areas of a robotic surgical instrument at the same time, while submerged in an ultrasonic cleaner.

BACKGROUND

Robotic and other laparoscopic type surgical instruments have been in use for over a decade. In general, one or more small incisions are made in the patient and an operating device, such as a scope, or other instrument, is fed through the incision(s), until the surgical device(s) and/or instrument(s) reaches the site of the operation. The inserted portions of the robotic surgical instruments are typically tubular in shape. In some examples, the robotic or laparoscopic instrument is a scalpel, scissors, or other cutting device for removal or repair of diseased or malfunctioning tissue. Advances in surgical systems and surgical instruments have greatly reduced operation times as well as recovery times; such as the removal of a gallbladder, etc.

U.S. Pat. No. 5,630,436 (hereafter '436) describes one method of cleaning that has effectively cleaned the interiors and exteriors of channeled tubular surgical instruments, such as orthoscopic/laparoscopic/endoscopic/and bone reamers. The '436 patent utilizes ultrasonic transducers affixed to the bottom of an ultrasonic tank that has been filled with cleaning solution, wherein the ultrasonic waves induce the separation of debris from the soiled instrument(s) placed in the ultrasonic bath. Further, in '436, the ultrasonic tank is attached to an independent suction apparatus that works simultaneously to suction out the loosened debris from the interior and tool end of a channeled tubular surgical instrument while it is being cleaned in the ultrasonic bath. More recently, this is accomplished by inserting just the distal tool end of the channeled tubular surgical instrument through a hole in the capped, individually dedicated, inline maximizing suction cleaning chamber, inline filter, inline pump, and inline fluid return tube that returns the filtered ultrasonic tank cleaning solution back to the ultrasonic bath wherein the attached channeled tubular surgical instrument is laying on the bottom of the fluid filled activated ultrasonic tank. The current configuration of the '436 can individually clean up to six channeled tubular surgical instruments at the same time using this well established cleaning system.

The combined surgical instrument cleaning methods of '436 have been used successfully in cleaning many types of flow through channeled tubular surgical instruments. However, this singular hookup method for cleaning channeled tubular surgical instruments in the '436 is incapable of adequately cleaning Robotic tubular surgical instruments, such as the da Vinci@ robotic surgical instruments manufactured by Intuitive Surgical, Inc., because one or more tight seals have been placed as a barrier between the distal tool end and the proximal shaft/control box end of the channeled areas within the robotic instrument in an effort to curtail the amount of bio burden at the tool end from migrating up into the segmented shaft/control box end; which reduces but does not totally prevent bio burden from migrating into the segmented proximal end of the robotic instrument.

The typical institutional practice for cleaning the distal tool end of a robotic surgical instrument is to scrub it by hand; which is time consuming, tedious, potentially dangerous, and can lead to liability and workman's compensation issues.

What is needed is a safer more cost effective automated way to clean both the distal and the proximal segmented areas of robotic surgical instruments.

SUMMARY

In one embodiment, an apparatus for cleaning robotic surgical instruments is disclosed, the apparatus including an ultrasonic emersion tank having cleaning fluid there within and a device for providing negative pressure (e.g. suction from a pump) through a tool-end cleaning chamber (preferably through a filter). Cleaning fluid is drawn into the tool-end cleaning chamber through a plurality of orifices in the tool-end cleaning chamber by the suction, thereby creating turbulence around a tool-end of a robotic surgical instrument inserted into the tool-end cleaning chamber. Since some robotic surgical instruments have very efficient seals at the tool-end, in addition to the cleaning chamber, the control end of the robotic surgical instruments is connected to a second source of negative pressure (e.g. suction from a pump) which circulates the cleaning fluid through all accessible areas of the control end and shaft of the robotic surgical instrument.

In another embodiment, a method of cleaning robotic surgical instruments is disclosed including inserting a tool-end of a robotic surgical instrument into a tool-end cleaning chamber and immersing the robotic surgical instrument and the tool-end cleaning chamber into cleaning fluid within an ultrasonic emersion tank. Next, negative pressure (suction) is applied to an orifice of the tool-end cleaning chamber, thereby causing flow of the cleaning fluid into the tool-end cleaning chamber through a plurality of ports, creating turbulence within the tool-end cleaning chamber. The control end of the robotic surgical instruments is cleaned by connecting a second source of negative pressure (e.g. suction from a pump) to the control end of the robotic surgical instrument. This suction circulates the cleaning fluid through all accessible areas of the control end and shaft of the robotic surgical instrument.

In another embodiment, apparatus for cleaning robotic surgical instruments is disclosed including an ultrasonic emersion tank having cleaning fluid there within. A device for providing negative pressure or suction (e.g. a pump) pulls cleaning fluid though a tool-end cleaning chamber and a filter, and cleaning fluid is drawn into the tool-end cleaning chamber through a plurality of orifices in the tool-end cleaning chamber by the negative pressure (suction), thereby creating turbulence around a tool-end of a robotic surgical instrument inserted into the tool-end cleaning chamber. Coupled to the ultrasonic tank is a device for creating ultrasonic waves within the cleaning fluid. Since some robotic surgical instruments have very efficient seals at the tool-end, in some embodiments, the control end of the robotic surgical instruments is connected to a second source of negative pressure (e.g. suction from a pump) which circulates the cleaning fluid through all accessible areas of the control end and shaft of the robotic surgical instrument.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
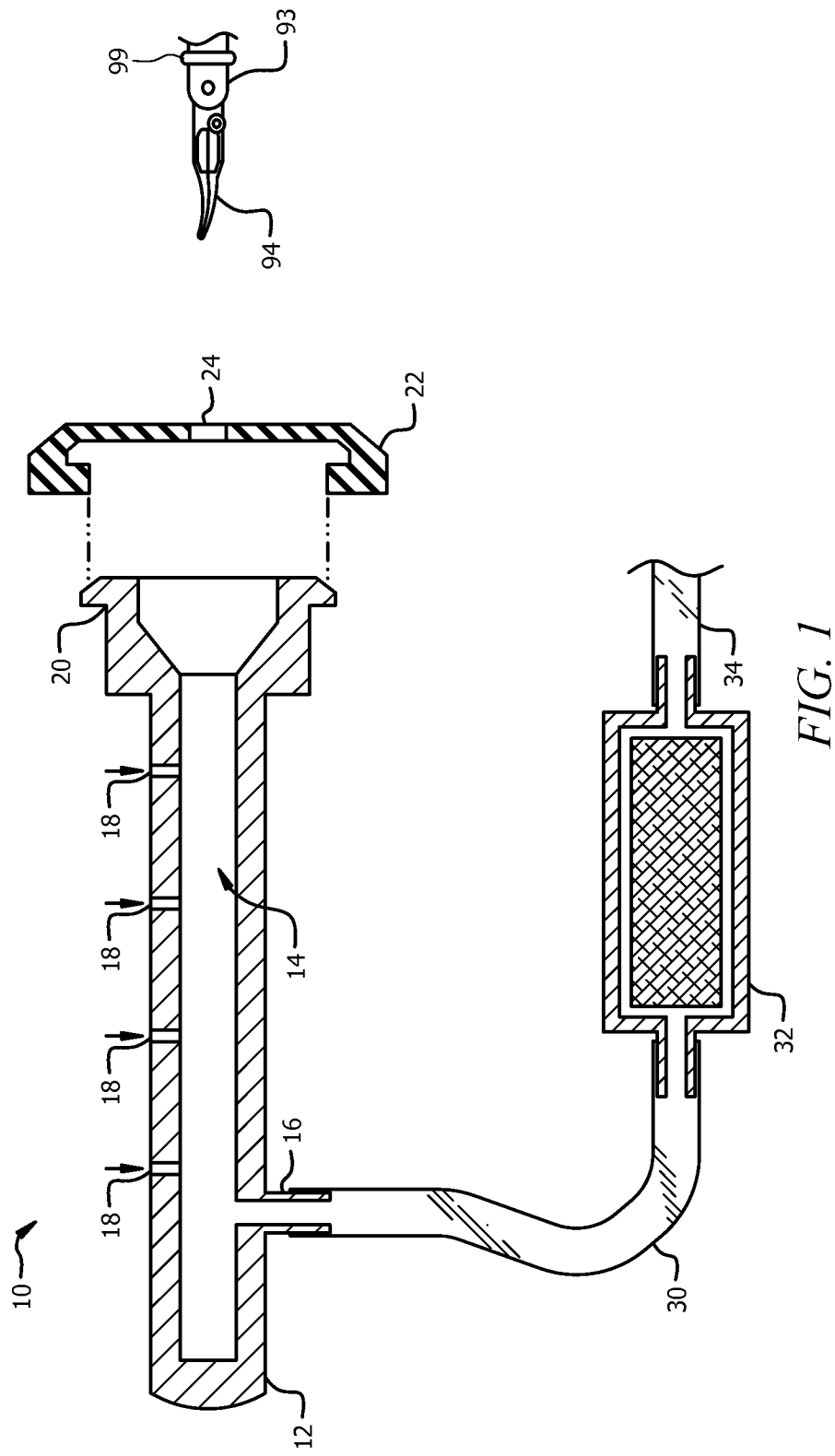
FIG. 1 illustrates a cut-away view of a tool-end cleaning chamber of a system for cleaning robotic surgical instruments.

Reference will now be made in detail to the presently preferred embodiments of the invention, examples of which are illustrated in the accompanying drawings. Throughout the following detailed description, the same reference numerals refer to the same elements in all figures.

The system for cleaning robotic surgical instruments is shown and described in use with one specific soiled instrument, e.g., as shown a daVinci@ robotic surgical instrument. This is one of the many different soiled instruments that system for cleaning robotic surgical instruments will clean and is shown as an example of such, not to be taken as limiting in any way. In general, such instruments are anticipated to be of generally elongated shape, though not required to be such. Also, such instruments are also anticipated to have tubular shafts with a control portion at one end of the shaft and a tool-end portion at an opposing end of the shaft, but again, there is no specific limitation on the overall shape, geometry, or size of the instruments to be cleaned.

The system for cleaning robotic surgical instruments operates on four base principles: immersing the soiled instrument in a cleaning solution; dislodging debris from the soiled instruments using ultrasonic waves; pumping fluid away from the instrument so that dislodged debris will flow out of the instrument and be captured in filters; and fluid jet cleaning of the tool-end of the instrument; as will be shown in the description related to the drawings. By pumping fluid away from the both ends to the robotic surgical instruments, any dislodged debris is pulled out of the robotic surgical instruments and trapped in a filter, rather than being pushed back into the robotic surgical instruments where is may get further lodged and, hence, not cleaned sufficiently.

Referring to FIG. 1, a cut-away view of a tool-end cleaning chamber 10 of a system for cleaning robotic surgical instruments 90/92/93/94/96/98/99 (see FIGS. 1-4) is shown. The tool-end cleaning chamber 10 comprises a body 12 that has a hollow core 14 that is preferably of a diameter slightly larger than a diameter of the expected tool-end 93/94, a suction attachment port 16, and an open receptor end 20. The tool-end cleaning chamber 10 is made of any suitable material such as a solid material that resists oxidation and accumulation of debris for example stainless steel or a hard plastic. The open end 20 of the tool-end cleaning chamber 10 engages with a flexible nipple 22 or cover 22. The flexible nipple 22 has an orifice 24, through which the tool-end 93/94 of a soiled surgical instrument is inserted, forming a seal around the shaft 92 of the robotic surgical instrument 90/92/93/94/96/98/99. The tool-end 93/94 is the end which typically is inserted into the patient for cutting of tissue, etc., and the tool-end 93/94 typically acquires a large share of the body tissue and fluids during an operation.

Figure 2:
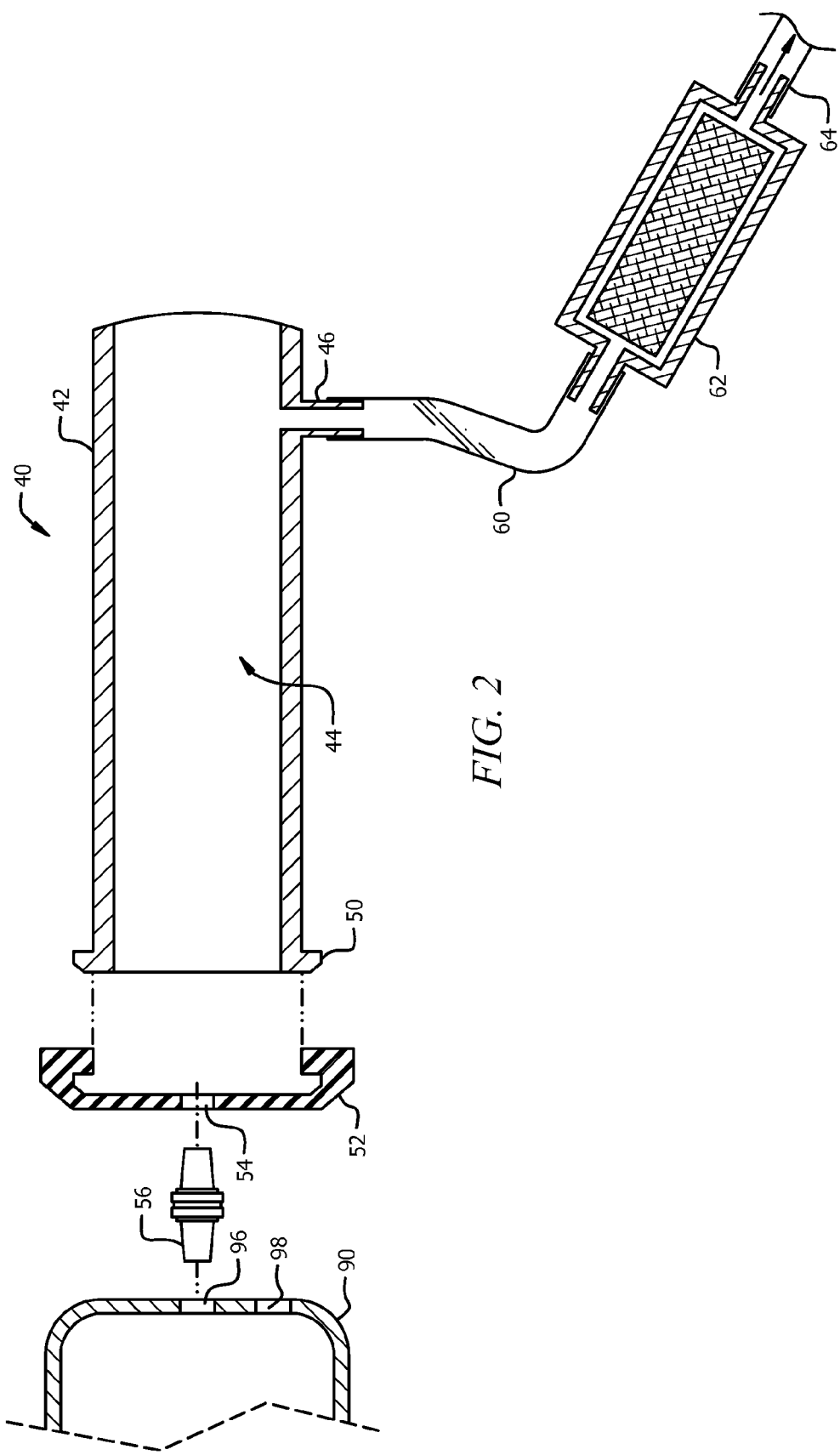
FIG. 2 illustrates a cut-away view of a control box/shaft-end cleaning chamber of the system for cleaning robotic surgical instruments.

Note that many robotic surgical instruments 90/92/93/94/96/98/99 have a very effective seal 99, through which it is difficult or impossible to flow materials through (e.g. between the tool-end 93/94 and the shaft 92) and, therefore, the tool-end 93/94 needs to be cleaned separately from the shaft 92 and the control box/shaft-end 90/92/96/98, which is cleaned from ports 96/98 on the control box 90 as described with FIG. 2.

The tool-end cleaning chamber 10 has a plurality of intake holes 18 are formed in the body 12. The intake holes 18 are sized and spaced in such a way that, as negative pressure (suction) is applied to the suction port 16 through suction tubes 30/34 and, preferably, a filter 32, cleaning fluids 104 from the ultrasonic emersion tank 100 (see FIG. 3), flow through the intake holes 18 and into the hollow core 14, creating turbulence that, in conjunction with or separate from the ultrasonic waves, dislodges debris from the tool-end 93/94. As debris is dislodged, the suction pulls the debris out the suction port 16 where it flows into the filter 32 and is trapped in the filter's media.

By keeping the hollow core 14 as narrow as to provide enough clearance for the tool-end 93/94 to fit, the turbulence and flow created by the cleaning fluid 104 being drawn in through the intake holes 18 concentrates in areas of the tool-end 93/94 that is mostly soiled. Although the intake holes 18 are shown on one side of the body 12 and equally spaced, any configuration of intake holes 18 is anticipated to provide ample flow through the intake holes 18, causing flow and turbulence which results in improved cleaning.

Referring to FIG. 2, a cut-away view of a control-end cleaning chamber 40 of a system for cleaning robotic surgical instruments 90/92/93/94/96/98/99 is shown. Some systems for cleaning robotic surgical instruments 90/92/93/94/96/98/99 are equipped to clean other types of surgical instruments (not shown) that permit flow of fluids in one end and out the other, as described in U.S. Pat. No. 5,630,436. In such, one end of this type of surgical instrument (not shown) is inserted into a cleaning chamber 40 similar to that shown in FIG. 2 and, as suction is drawn from the suction tube 60, fluids flow in to this surgical instrument (not shown) from an end distal to the cleaning chamber 40. Being that the seals on certain robotic surgical instruments 90/92/93/94/96/98/99 are very robust, this flow is not possible. Therefore, the control box 90 and shaft 92 need to be cleaned by flowing fluid through the control box 90 and shaft 92 from the control box 90.

In one embodiment, it is anticipated that the suction tube 60 is connected directly to an orifice 96 on the control box 90 of the robotic surgical instrument 90/92/93/94/96/98/99 by, for example, a male-male fitting 56 (not shown).

In another embodiment, because other types of surgical instruments (not shown) are often cleaned using a control box/shaft-end cleaning chamber 40 similar to that shown in FIG. 2, the same control box/shaft-end cleaning chamber 40 is used. By using the same control box/shaft-end cleaning chamber 40, little or less disassembly and reassembly is required when switching between cleaning of different surgical instruments. Therefore, it is preferred to attach the control box/shaft-end cleaning chamber 40 to the orifice 96 on the control box 90 of the robotic surgical instrument 90/92/93/94/96/98/99. In such, the control box/shaft-end cleaning chamber 40 comprises a body 42 that has a hollow core 44, a suction attachment port 46, and an open receptor end 50. The control box/shaft-end cleaning chamber 40 is also made of any suitable material such as stainless steel. The open end 50 of control-end cleaning chamber 40 engages with a second flexible nipple 52 (or cover). The second flexible nipple 52 has an orifice 54, through which a first end of a male-male fitting 56 is inserted. An opposing end of the male-male fitting 56 interfaces with a port 96 on the control box 90 of the robotic surgical instrument 90/92/93/94/96/98/99.

As negative pressure (e.g. suction) is applied to the suction port 46 through suction tubes 60/64 and, preferably, a filter 62, cleaning fluids 104 from the ultrasonic emersion tank 100 (see FIG. 3), flow into, for example, an orifice 98 of the control box 90 of the robotic surgical instrument 90/92/93/94/96/98/99, through inner channels and shaft 92 of the robotic surgical instrument 90/92/93/94/96/98/99, out the orifice 96 of the control box 90, through the male-male fitting 56 and into the hollow core 44. As ultrasonic waves dislodge debris from the internal channels (e.g. of the shaft 92) of the robotic surgical instrument 90/92/93/94/96/98/99, the negative pressure (suction) pulls the debris out the suction port 46 where it flows into the filter 62 where the debris is trapped in the filter's media.

Figure 3:
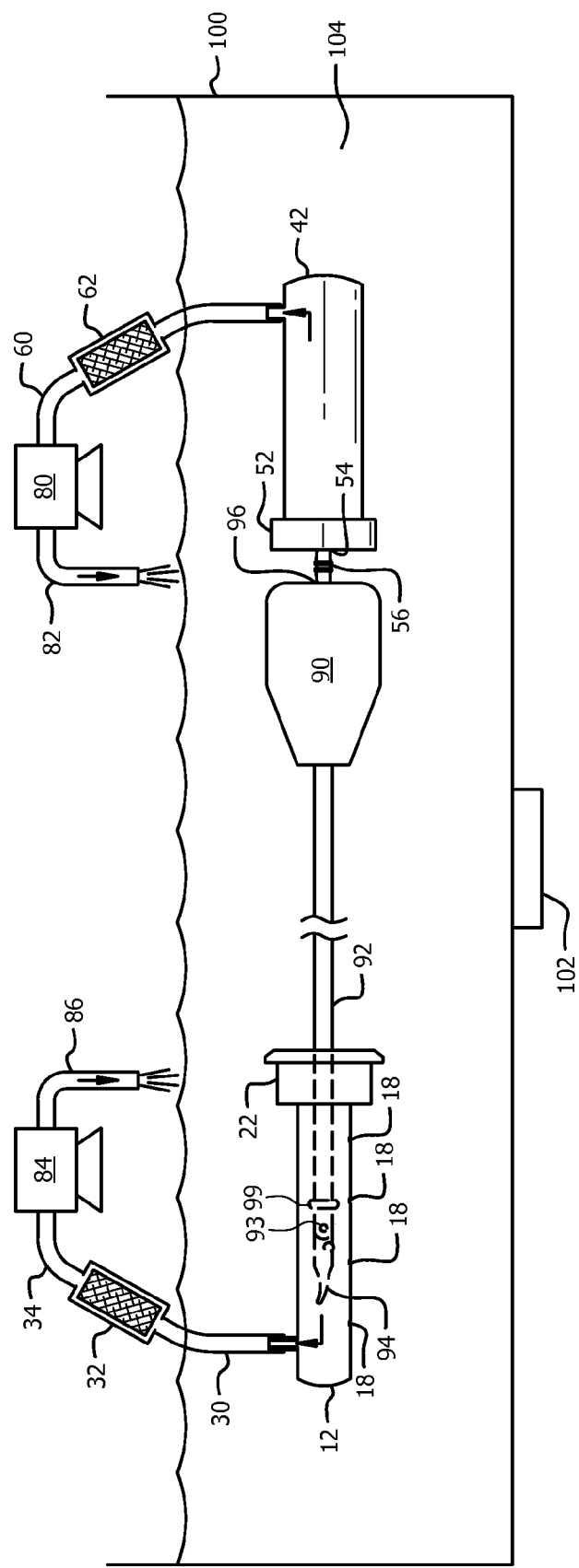
FIG. 3 illustrates a plan view of the system for cleaning robotic surgical instruments.

Referring to FIG. 3, a plan view of the system for cleaning robotic surgical instruments 90/92/93/94/96/98/99 is shown. The tool-end 93/94 of a soiled robotic surgical instrument 90/92/93/94/96/98/99 is shown inserted into the tool-end cleaning chamber 10, passing through the orifice 24 in the flexible nipple 22. As suction (negative pressure) is pulled from the suction attachment port 16 of the tool-end cleaning chamber 10, cleaning fluid 104 flows into the hollow core 14 of the tool-end cleaning chamber 10 through the plurality of intake holes 18, creating turbulence within the hollow core 14, thereby dislodging debris from the tool-end 93/94, which debris flows along the path of the suction through the suction tube 30 and is trapped within the optional filter 32. The filter is operatively connected to a source of negative pressure (suction) such as a pump 84, by a continuing tube 34. As the pump operates and receives fluid from the filter 32 and tube 34, the fluid is recirculated into the ultrasonic emersion tank 100 through an exit tube 86.

The male-male fitting 56 is shown interfacing between the orifice of the 54 of the second flexible nipple 52 and the orifice 96 on the control box/shaft-end 90 of the robotic surgical instrument 90/92/93/94/96/98/99. As suction is pulled from the suction port 46 by a second pump 80 (or in some embodiment, the same pump 84), debris from within the soiled robotic surgical instrument 90/92/93/94/96/98/99 is pulled through suction tube 60 and is captured by a filter 62. After passing through the pump 80, the fluid is recirculated back into the ultrasonic emersion tank 100 through an exit tube 82.

During cleaning, it is preferred that the entire robotic surgical instrument 90/92/93/94/96/98/99 is submerged within the cleaning fluid 104 of the ultrasonic emersion tank 100. In this, ultrasonic waves from the ultrasonic emitting device 102 will vibrate debris from the surfaces of the robotic surgical instrument 90/92/93/94/96/98/99.

Figure 4:
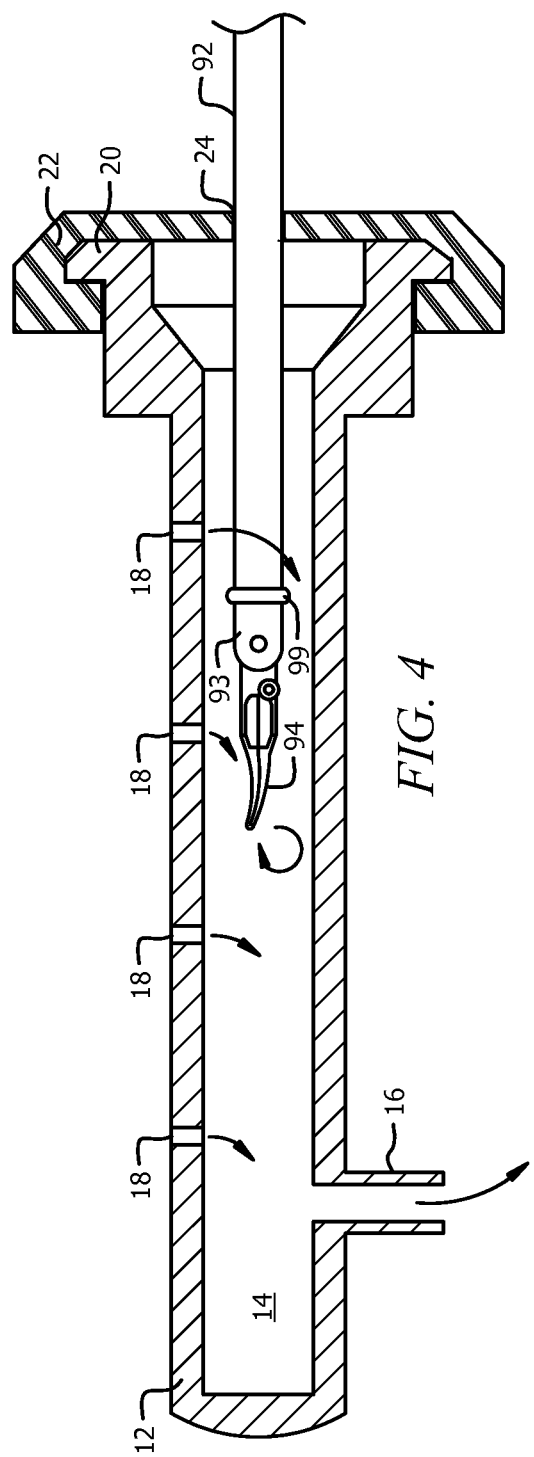
FIG. 4 illustrates a cut-away view of a tool-end cleaning chamber of the system for cleaning robotic surgical instruments having there within a tool-end of a robotic surgical instrument.

Referring to FIG. 4, a cut-away view of a tool-end cleaning chamber 10 of the system for cleaning robotic surgical instruments 90/92/93/94/96/98/99 having there within placed an tool-end of a robotic surgical instrument 90/92/93/94/96/98/99 is shown. The tight fit between the orifice 24 of the flexible nipple 22 attached to the opening 20 of the tool-end cleaning chamber 10 and the extended shaft 92 of the robotic surgical instrument 90/92/93/94/96/98/99 is visible in FIG. 4. As negative pressure (suction) is applied to the suction port 16 through suction tubes 30/34 and the filter 32, cleaning fluids 104 from the ultrasonic emersion tank 100, flow into the hollow core 14 through the intake holes 18 and into the hollow core 14, forming turbulence (shown as looping arrows). As the ultrasonic waves and the turbulent flow dislodge debris from the tool-end 93/94 of the robotic surgical instrument 90/92/93/94/96/98/99, the suction pulls the debris out the suction port 16 where the debris flows into and is trapped in the filter 32. The remaining cleaning fluid 104 flows through the pump 84 and is returned back into the ultrasonic emersion tank 100.

It is anticipated that any number of pumps 80/84 are used, including one pump 80. Likewise, it is anticipated that any number of filters 32/62 are used, including one filter 32. It is also anticipated that multiple robotic surgical instrument 90/92/93/94/96/98/99 be cleaned simultaneously within the same ultrasonic emersion tank 100, providing multiple sets of tool-end cleaning chambers 10 and control box/shaft-end cleaning chambers 40, with as many pumps 80/84 and filters 32/62 as needed.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely for example and showing explanatory embodiment thereof. It is the intention of the following claims to encompass and include such changes.

What is claimed is:

1. An apparatus for cleaning robotic surgical instruments, the apparatus comprising:
    an ultrasonic immersion tank having a transducer that emits ultrasonic waves;
    cleaning fluid within the ultrasonic immersion tank;
    a pump;
    a tool-end cleaning chamber fluidly interfaced to the pump through a suction attachment port on one side of a body of the tool-end cleaning chamber, the tool-end cleaning chamber filled with the cleaning fluid, whereas, as the pump pulls the cleaning fluid from within the tool-end cleaning chamber, the cleaning fluid is drawn into the tool-end cleaning chamber solely through a plurality of intake holes in body of the tool-end cleaning chamber, the intake holes aligned in linear fashion on a second lengthwise side of the tool-end cleaning chamber, the second lengthwise side of the tool-end cleaning chamber being opposite to the one side of the body of the tool-end cleaning chamber, thereby creating turbulence for cleaning a tool-end of a robotic surgical instrument that has been inserted into the tool-end cleaning chamber and whereas the ultrasonic waves dislodge debris from the tool-end of the robotic surgical instrument; and
    a control box/shaft-end cleaning chamber and a second pump, the control box/shaft-end cleaning chamber has a fitting that interfaces into an orifice of a control box of the robotic surgical instrument such that the cleaning fluid is drawn into the control box of the robotic surgical instrument through a second orifice, the cleaning fluid is pulled through a shaft of the robotic surgical instrument, the cleaning fluid is pulled out of the orifice, then the cleaning fluid is pulled through the control box/shaft-end cleaning chamber by the second pump.

2. The apparatus for cleaning robotic surgical instruments of claim 1, wherein debris from the tool-end of the robotic surgical instrument is captured by a filter before the cleaning fluid is returned from the pump back into the ultrasonic immersion tank.

3. The apparatus for cleaning robotic surgical instruments of claim 1, wherein the tool-end cleaning chamber is made of steel; and wherein the ultrasonic immersion tank comprises a tank, the tank at least partially filled with the cleaning fluid, and an ultrasonic emitter operatively coupled to the tank such that the ultrasonic emitter emits ultrasonic waves that flow through the cleaning solution within the tank, thereby dislodging debris from the robotic surgical instrument.

4. The apparatus for cleaning robotic surgical instruments of claim 1, further comprising a second filter, the second filter removing debris from the cleaning fluid after the cleaning fluid exits the control box/shaft-end cleaning chamber and before the cleaning fluid returns to the ultrasonic immersion tank.

5. The apparatus for cleaning robotic surgical instruments of claim 1, wherein fitting is a male-male fitting.

6. The apparatus for cleaning robotic surgical instruments of claim 1, wherein the tool-end cleaning chamber has a hollow body made of steel and the tool-end cleaning chamber has an open end, the open end covered by a flexible nipple cap having an orifice through which the tool-end of the robotic surgical instrument is inserted.

7. The apparatus for cleaning robotic surgical instruments of claim 5, wherein the control box/shaft-end cleaning chamber has a hollow body made of steel and the control box/shaft end cleaning chamber has an open end, the open end covered by a second flexible nipple, the second flexible nipple having an orifice through which an end of the male-male fitting is coupled.

8. An apparatus for cleaning robotic surgical instruments, the apparatus comprising:
   an ultrasonic immersion tank;
   cleaning fluid within the ultrasonic immersion tank;
   a pump;
   a tool-end cleaning chamber fluidly interfaced to the pump through a suction attachment port on one side of a body of the tool-end cleaning chamber, the tool-end cleaning chamber submerged in the cleaning fluid, the tool-end cleaning chamber filled with the cleaning fluid, whereas, cleaning fluid is drawn into the tool-end cleaning chamber through a plurality of intake holes the intake holes aligned in linear fashion on a lengthwise second side of the body of the tool-end cleaning chamber by the pump, the lengthwise second side being opposite to the one side of the body of the tool-end cleaning chamber, thereby creating a flow of the cleaning fluid across a tool-end of a robotic surgical instrument inserted into the tool-end cleaning chamber;
   an ultrasonic generator interfaced to the ultrasonic immersion tank such that ultrasonic waves from the ultrasonic generator dislodge debris from the tool end of the robotic surgical instrument inserted into the tool-end cleaning chamber; and
   a second pump fluidly interfaced to a first orifice of a control box of the robotic surgical instrument through a fitting that has a first side inserted into the first orifice and a second side interfaced to the second pump such that the cleaning fluid is drawn into the robotic surgical instrument through a second orifice of the control box, the cleaning fluid is pulled through the control box, the cleaning fluid is pulled through a shaft of the robotic surgical instrument, and the cleaning fluid is pulled out of the first orifice.

9. The apparatus for cleaning robotic surgical instruments of claim 8, wherein walls of the tool-end cleaning chamber are made of steel for conducting the ultrasonic waves from the fluid in the ultrasonic immersion tank to the fluid within the tool-end cleaning chamber.

10. The apparatus for cleaning robotic surgical instruments of claim 8, wherein debris from the end of the robotic surgical instrument is captured by a filter before the cleaning fluid is returned back into the ultrasonic immersion tank.

11. The apparatus for cleaning robotic surgical instruments of claim 9, further comprising a second filter, the second filter removing debris from the cleaning fluid after the cleaning fluid exits the first orifice and before the cleaning fluid returns to the ultrasonic immersion tank.

* * * * *